United States Patent
Kim et al.

(10) Patent No.: US 9,061,022 B2
(45) Date of Patent: Jun. 23, 2015

(54) **PHARMACEUTICAL COMPOSITION FOR TREATING WOUNDS OR REVITALIZING SKIN COMPRISING *EUPHORBIA KANSUI* EXTRACTS, FRACTIONS THEREOF OR DITERPENE COMPOUNDS SEPARATED FROM THE FRACTIONS AS ACTIVE INGREDIENT**

(71) Applicant: KOREA RESEARCH INSTITUTE OF BIOSCIENCE AND BIOTECHNOLOGY, Daejeon (KR)

(72) Inventors: Jae Wha Kim, Daejeon (KR); Sei Ryang Oh, Daejeon (KR); Kyung Seop Ahn, Daejeon (KR); Ho Bum Kang, Daejeon (KR); Ok-Kyoung Kwon, Daejeon (KR); Seung Ho Kim, Daejeon (KR); Jang Mi Son, Daejeon (KR); Hyuk Hwan Song, Daejeon (KR); Hee Gu Lee, Daejeon (KR); Byeong Hwa Jeon, Daejeon (KR); Da Jung Ji, Daejeon (KR); Khiev Piseth, Daejeon (KR)

(73) Assignee: Korea Research Institute of Bioscience And Biotechnology, Daejeon (KR)

( * ) Notice: Subject to any disclaimer, the term of this patent is extended or adjusted under 35 U.S.C. 154(b) by 0 days.

(21) Appl. No.: 14/559,254

(22) Filed: Dec. 3, 2014

(65) Prior Publication Data

US 2015/0093456 A1 Apr. 2, 2015

Related U.S. Application Data

(63) Continuation of application No. PCT/KR2013/005131, filed on Jun. 11, 2013.

(30) Foreign Application Priority Data

Jun. 11, 2012 (KR) .................... 10-2012-0062231

(51) Int. Cl.
*A01N 65/00* (2009.01)
*A61K 36/47* (2006.01)
*A61K 31/215* (2006.01)
*A61K 36/00* (2006.01)

(52) U.S. Cl.
CPC .............. *A61K 36/47* (2013.01); *A61K 31/215* (2013.01); *A61K 36/00* (2013.01)

(58) Field of Classification Search
CPC ..................................................... A61K 36/00
USPC ......................................................... 424/725
See application file for complete search history.

(56) References Cited

FOREIGN PATENT DOCUMENTS

| CN | 1698829 A | 11/2005 |
|---|---|---|
| JP | 08-175957 A | 7/1996 |
| KR | 10-2009-0036210 A | 4/2009 |
| KR | 10-2012-0057943 A | 6/2012 |

OTHER PUBLICATIONS

O. James, et al; Phytochemical composition, bioactivity and wound . . . ; Int. Journ. Pharm. Biomedical Research; vol. 1; No. 1; 2010; pp. 54-63.
P. Bigoniya, et al; Protective effect of *Euphorbia neriifolia* saponin fraction . . . ; African-Journal of Biotechnology; vol. 9; No. 42; 2010; pp. 7148-7156.
J.S. Chang, et al; Kansuinine A and kansuinine B from *Euphorbia kansui* . . . ; Planta Med.; vol. 76, 2010; pp. 1544-1549.

*Primary Examiner* — Michael Meller
(74) *Attorney, Agent, or Firm* — Lucas & Mercanti, LLP

(57) ABSTRACT

The present invention relates to a pharmaceutical composition for treating wounds or revitalizing skin comprising the *Euphorbia kansui* extract, the fractions thereof, or the diterpene compound isolated therefrom as an active ingredient. The *Euphorbia kansui* extract may act on epithelial cells to induce PKD1 activity required for improving the reproduction capability of differentiated epithelial cells, and thus may induce the phosphorylation of lower ERK1 and the generation of Cycline D, thus exhibiting an excellent ability to activate the reproduction of damaged skin. Therefore, the *Euphorbia kansui* extract may be used effectively as an active ingredient in a pharmaceutical composition for treating wounds or reproducing skin, a health food for recovering skin damage or reproducing skin, or a functional cosmetic for inducing skin cell activity.

1 Claim, 6 Drawing Sheets

PHARMACEUTICAL COMPOSITION FOR TREATING WOUNDS OR REVITALIZING SKIN COMPRISING *EUPHORBIA KANSUI* EXTRACTS, FRACTIONS THEREOF OR DITERPENE COMPOUNDS SEPARATED FROM THE FRACTIONS AS ACTIVE INGREDIENT

CROSS-REFERENCE TO RELATED APPLICATIONS

This application is a continuation of PCT/KR2013/005131, filed Jun. 11, 2013, which claims the benefit of Korean Patent Application No. 10-2012-0062231, filed Jun. 11, 2012, the contents of each of which are incorporated herein by reference.

BACKGROUND OF THE INVENTION

1. Field of the Invention

The present invention relates to a pharmaceutical composition for treating wounds or reproducing skin comprising the *Euphorbia kansui* extract, the fractions thereof, or the diterpene compound isolated therefrom as an active ingredient.

2. Description of the Related Art

The *Euphorbia kansui* extract has been known, according to the traditional oriental medicine, to have cardiotonic activity, diarrhea inducing activity (stimulating intestines to promote peristaltic motion and to cause diarrhea), diuretic effect, and anti-inflammatory activity, and to be effective in treating swelling, hydrops abdominis, short of breath, difficulty in discharging urine, dropsy, ascites (pondong), beriberi, dyspnea with cough, pleuritis, heart pain, jaundice, malaria, chronic indigestion, swelling/bloating, water brash, chest bind, diabetes, paresthesia with pain, illeus and urinary disorder, epilepsy, esophageal cancer, and wet pleurisy, and also has been known as an ingredient of a medicine for discharging urine and for inducing diarrhea. However, the biological activity of the extract has not been clearly explained, yet.

The reproduction of epithelial cell is a very important factor for wound-healing. It has been recently disclosed that the cell activity related to the reproduction of epithelial cell is based on the activities of PKD1 and ERK1 (J Biol Chem. 2010 Jul. 23; 285(30):23387-97. Epub 2010 May 12. Nature, 2008 May 15; 453(7193):314-21: J Biol Chem, 2005 Sep. 30; 280(39):33262-9. Epub 2005 Jul. 8). Based on the previous report concerning the analysis of the changes in skin tissues investigated in order to examine the reproduction of damaged skin, the active materials working on the wounded skin are EGF, FGF, and HGF, which are known as the cell scattering factors to increase cell migration (EMBO J. 2011 Feb. 16; 30(4):783-95. Epub 2011 Jan. 11:Mol Physiol, 2010 June; 298(6):L715-31:J Eur Acad Dermatol Venereol, 2011 Dec. 26. doi: 10.1111/j.1468-3083.2011.04415.x). There have been attempts made to identify a natural material from an extract of a natural substance that has the ability to induce the generation of such active materials to revitalize the damaged epithelial cells. That is, a novel natural material that is effective in wound-healing has been developed among the extracts of natural substances based on physiological basis. However, there is no report yet to say that the *Euphorbia kansui* extract or the fractions thereof is effective in inducing the activation of epithelial cells or in wound-healing.

In the course of study to develop a natural drug effective in wound-healing, the present inventors confirmed through animal test that the *Euphorbia kansui* extract was excellent in increasing the cell migration activity of HGF, the intrinsic factor of epithelial cell, in inducing the activation of PKE1 and the phosphorylation of ERK1 which are the basic cell signaling systems having intracellular activity, and in promoting recovery from would, suggesting that the said extract had the activity of recovering skin damage or reproducing skin, leading to the completion of the present invention.

SUMMARY OF THE INVENTION

It is an object of the present invention to provide a pharmaceutical composition for treating wounds or reproducing skin comprising the *Euphorbia kansui* extract, the fractions thereof, or the diterpene compound isolated from the same as an active ingredient, or a health food for recovering skin damage or reproducing skin, or a cosmetic composition comprising the same for the same purpose.

It is another object of the present invention to provide a method for treating wounds or reproducing skin containing the step of administering the *Euphorbia kansui* extract, the fractions thereof, or the diterpene compound isolated from the same to a subject with skin damage.

It is also an object of the present invention to provide a use of the *Euphorbia kansui* extract, the fractions thereof, or the diterpene compound isolated therefrom for a pharmaceutical composition for treating wounds or reproducing skin.

It is further an object of the present invention to provide a use of the *Euphorbia kansui* extract, the fractions thereof, or the diterpene compound isolated therefrom for a cosmetic composition for recovering skin damage or reproducing skin.

To achieve the above objects, the present invention provides a pharmaceutical composition for treating wounds or reproducing skin comprising the *Euphorbia kansui* extract or the fractions thereof as an active ingredient.

The present invention also provides a health food or a cosmetic composition for recovering skin damage or reproducing skin comprising the *Euphorbia kansui* extract or the fractions thereof as an active ingredient.

The present invention further provides a method for treating wounds or reproducing skin containing the step of administering the *Euphorbia kansui* extract or the fractions thereof to a subject with skin damage.

The present invention also provides a use of the *Euphorbia kansui* extract or the fractions thereof for a pharmaceutical composition for treating wounds or reproducing skin.

The present invention also provides a use of the *Euphorbia kansui* extract or the fractions thereof for a cosmetic composition for recovering skin damage or reproducing skin.

The present invention also provides a pharmaceutical composition for treating wounds or reproducing skin comprising at least one of the diterpene compounds represented by formula 1 or formula 2 or the pharmaceutically acceptable salts thereof as an active ingredient.

The present invention also provides a health food or a cosmetic composition for recovering skin damage or reproducing skin comprising at least one of the diterpene compounds represented by formula 1 or formula 2 or the pharmaceutically acceptable salts thereof as an active ingredient.

The present invention also provides a method for treating wounds or reproducing skin containing the step of administering at least one of the diterpene compounds represented by formula 1 or formula 2 or the pharmaceutically acceptable salts thereof to a subject with skin damage.

The present invention also provides a use of at least one of the diterpene compounds represented by formula 1 or formula 2 or the pharmaceutically acceptable salts thereof for a pharmaceutical composition for treating wounds or reproducing skin.

The present invention also provides a use of at least one of the diterpene compounds represented by formula 1 or formula 2 or the pharmaceutically acceptable salts thereof for a cosmetic composition for treating wounds or reproducing skin.

[Formula 1]

KC73-2

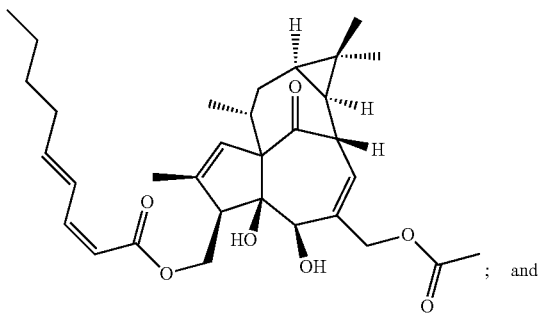

; and

[Formula 2]

KC16-20

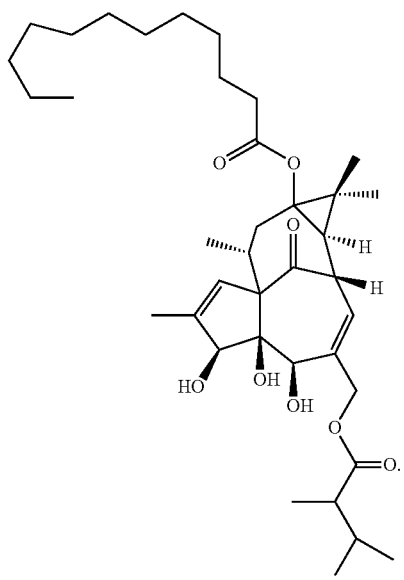

ADVANTAGEOUS EFFECT

The present invention relates to a pharmaceutical composition for treating wounds or revitalizing skin comprising the *Euphorbia kansui* extract, the fractions thereof, or the diterpene compound isolated therefrom as an active ingredient. The *Euphorbia kansui* extract may act on epithelial cells to induce PKD1 activity required for improving the reproduction capability of differentiated epithelial cells, and thus may induce the phosphorylation of lower ERK1 and the generation of Cycline D, thus exhibiting an excellent ability to activate the reproduction of damaged skin. Therefore, the *Euphorbia kansui* extract can be used effectively as an active ingredient in a pharmaceutical composition for treating wounds or reproducing skin, a health food for recovering skin damage or reproducing skin, or a functional cosmetic for inducing skin cell activity.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
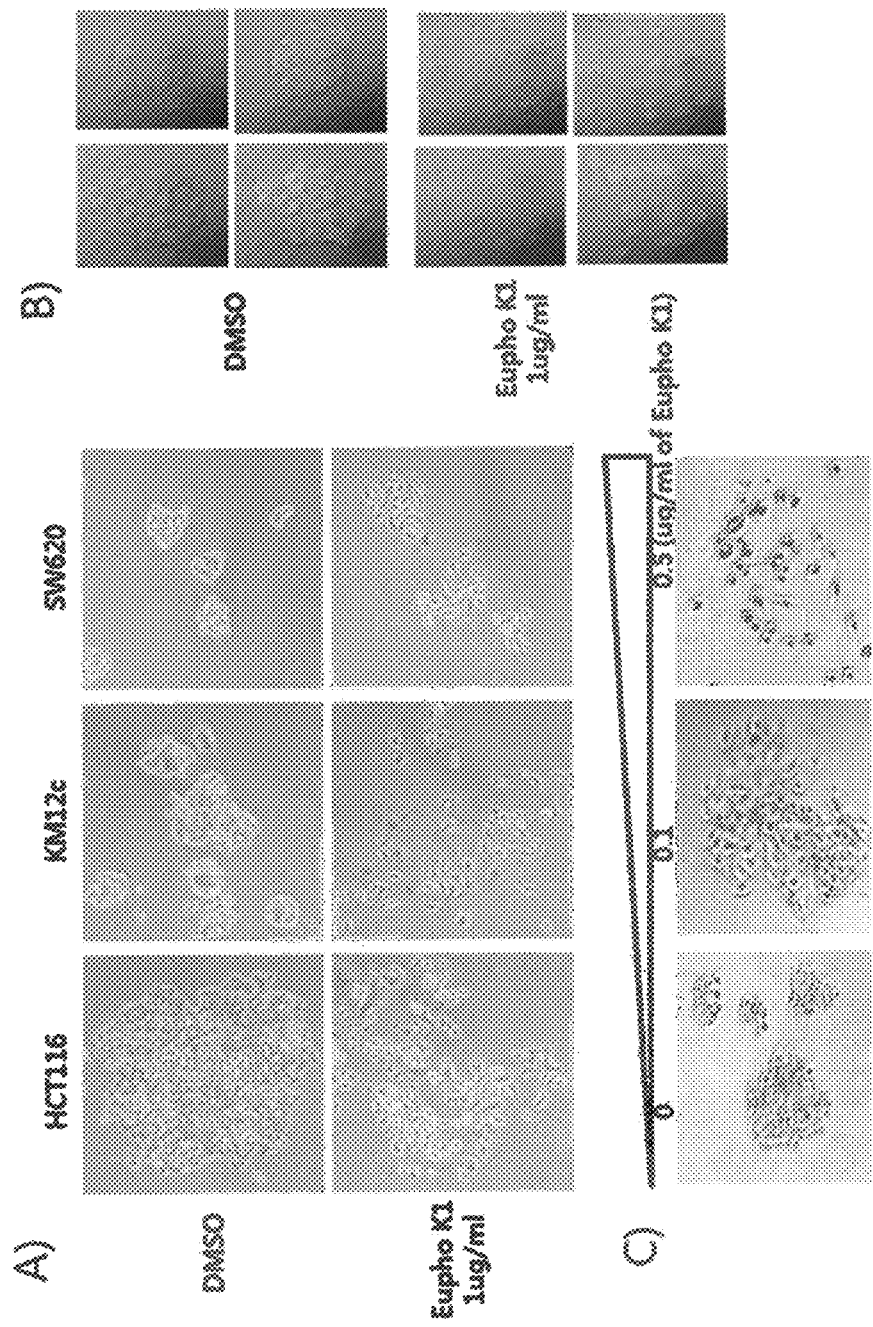
FIG. 1 is a diagram illustrating that cell migration was promoted in HCT116, KM12c, and SW620, the epithelial cells, treated with the *Euphorbia kansui* extract.

Hereinafter, the terms used in this invention are defined in more detail.

The term "improvement" or "improving" used in this invention indicates all the activity that can improve the symptoms of the disease or change them favorably by administering the composition of the present invention.

The term "administration" or "administering" used in this invention indicates the action of providing a certain amount of the composition of the present invention to a subject via a random but proper method. The administration pathway of the composition of the present invention can be any conventional pathway, either oral or parenteral pathway, as long as the composition can reach a target tissue. The composition can be administered via a random device suitable for the migration of the active ingredient into a target cell.

Hereinafter, the present invention is described in detail.

The present invention provides a pharmaceutical composition for treating wounds or reproducing skin comprising the *Euphorbia kansui* extract or the fractions thereof as an active ingredient.

The *Euphorbia kansui* extract is preferably prepared by the preparation method comprising the following steps, but not always limited thereto:
1) adding an extraction solvent to *Euphorbia kansui*, followed by extraction;
2) filtering the extract of step 1); and
3) concentrating the extract filtered in step 2) under reduced pressure, followed by drying thereof.

The *Euphorbia kansui* extract of step 1) can be either purchased or cultivated. Any part of *Euphorbia kansui*, for example roots, flowers, stems, leaves, or fruits, can be used, but roots are preferred, but not always limited thereto.

In the above method, the extraction solvent of step 1) is preferably water or $C_1$-$C_4$ lower alcohol, and the lower alcohol herein is ethanol or methanol. The extraction method herein is preferably shaking extraction, Soxhlet extraction, or reflux extraction, but not always limited thereto. The volume of the extraction solvent is preferably 2~20 times the dry weight of Euphorbia kansui. The extraction temperature is preferably 20° C.~50° C., but not always limited thereto. The extraction time is preferably 10~48 hours, and more preferably 24 hours, but not always limited thereto. The extraction is preferably performed with 3~5 repeats, and more preferably performed with 3 repeats, but not always limited thereto.

In the above method, the concentration under reduced pressure in step 3) is preferably performed by using a vacuum concentrator or a rotary evaporator, but not always limited thereto. In the above method, the drying process is preferably performed by low pressure drying, vacuum drying, boiling drying, spray drying, or freeze drying, but not always limited thereto.

The fractions herein can be obtained by using an organic solvent selected from the group consisting of acetone, ether, acetate, chloroform, butyl acetate, 1,3-butyleneglycol, hexane, and diethylether, but not always limited thereto.

The Euphorbia kansui extract or the fractions thereof preferably have the activity of treating wounds, recovering skin damage, or reproducing skin, but not always limited thereto.

In a preferred embodiment of the present invention, the inventors prepared the Euphorbia kansui extract and the fractions thereof. To investigate the capability of the Euphorbia kansui extract to induce epithelial cell scattering, the extract was treated to the epithelial cells, HCT116, KM12C, SW620, and Colo205. As a result, it was confirmed that the cell migration was induced by the treatment of the Euphorbia kansui extract (see FIG. 1).

The Euphorbia kansui extract was treated to the epithelial cells, HCT116, KM12C, SW620, and Colo205, and then the mRNA level of fibronectin, the intracellular factor known to induce cell migration, was measured. As a result, a significant change of the level was observed in SW620 (see FIG. 2A). This SW620 was observed for 6 hours, during which the level was continuously increased. The expression pattern of Zeb1, involved in the suppression of cell migration, was similar to that of the fibronectin (see FIG. 2B).

To confirm that the phosphorylations of PKD1 (protein kinase D1) and ERK (extracellular signal-regulated kinase), both involved in the activation of epithelial cells, were induced by the Euphorbia kansui extract, the extract was treated to the epithelial cell line SW620, followed by observation. As a result, PKD1 and ERK were up-regulated for 30 minutes after the treatment (see FIG. 3A).

To analyze the cell migration of epithelial cells in relation to wound-healing, matrigel analysis was performed to evaluate the vitality in trans-well. As a result, the effect was increased in the medium treated with the Euphorbia kansui extract (see FIG. 4).

To evaluate the activities caused by various cytokines secreted in wounded cells, matrigel analysis was performed. As a result the effect was increased in the medium treated with the Euphorbia kansui extract. When TGF was co-treated, the cell migration was even greater (see FIG. 5).

To investigate the skin reproduction effect of the Euphorbia kansui extract, skin damage was made on the shaved skin of Balb/C mouse by tape strapping. Then, the Euphorbia kansui extract was treated thereto. As a result, the recovery of skin damage was very fast, that is the skin turned back to normal fast after the wound-healing (see FIG. 6).

Therefore, the present invention confirmed and proved that the composition of the invention induced the phosphorylations of both PKD1 and ERK inducing the activation of epithelial cells on wounded skin and also had the effect of activating cell scattering in addition to the excellent wound-healing effect. So, the pharmaceutical composition of the present invention for treating wounds and reproducing skin can be effectively used for the treatment and prevention of wounds such as abrasion, incision, contusion, stab wound, laceration, and bite wound.

The composition of the present invention can be prepared by mixing with generally used diluents or excipients such as fillers, extenders, binders, wetting agents, disintegrating agents and surfactants.

Solid formulations for oral administration are tablets, pills, powders, granules, capsules, and troches. These solid formulations are prepared by mixing one or more compounds of the present invention with one or more suitable excipients such as starch, calcium carbonate, sucrose, lactose, or gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin.

Formulations for parenteral administration are sterilized aqueous solutions, water-insoluble excipients, suspensions, emulsions, lyophilized preparations and suppositories.

Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerol, gelatin, etc, but not always limited thereto.

The composition of the present invention is administered at a pharmaceutically effective dose. The term "pharmaceutically effective dose" herein indicates the amount enough to treat the disease with applicable, reasonable or risky concentration. The dose can be determined by considering many factors such as the kind of disease, severity of disease, activity of drug, drug sensitivity, administration frequency and pathway, excretion, term of treatment, co-treatment drug and other factors regarded as relevant in the medicinal field. The composition of the present invention can be administered as an individual agent or treated as combined with other agents. It can be administered with other drugs serially stepwise or simultaneously. It can also be one-time administration or multiple administrations. It is important in the administration of this composition to try to get the maximum effect with the minimum effective dose without side effects. This amount can be determined by those in the art.

Particularly, the effective dose of the Euphorbia kansui extract and the fractions thereof can be varied according to age, gender, and weight of patient. In general, the effective dose is 0.1~100 mg/kg, and more preferable dose 0.5~10 mg/kg, which can be administered daily or every other day, 1~3 times a day. However, this effective dose can be reduced or increased according to the administration pathway, severity of obesity, gender, weight, and age, and the effective dose of the composition cannot limit the spirit and scope of the present invention.

The present invention provides a cosmetic composition for recovering skin damage or reproducing skin comprising the *Euphorbia kansui* extract or the fractions thereof as an active ingredient.

The *Euphorbia kansui* extract or the fractions thereof might be supposed to have the activity of treating wound, recovering skin damage, or reproducing skin, but not always limited thereto.

The *Euphorbia kansui* extract or the fractions thereof of the present invention induced the phosphorylations of both PKD1 and ERK inducing the activation of epithelial cells on wounded skin and also had the effect of activating cell scattering in addition to the excellent wound-healing effect. Therefore, the pharmaceutical composition of the present invention for treating wounds and reproducing skin can be effectively used for the treatment and prevention of wounds such as abrasion, incision, contusion, stab wound, laceration, and bite wound.

The cosmetic composition for recovering skin damage or reproducing skin of the present invention can additionally include a supplement generally used in the field of cosmetics such as fatty substance, organic solvent, resolvent, concentrate, gelling agent, softener, antioxidant, suspending agent, stabilizer, foaming agent, odorant, surfactant, water, ionic or non-ionic emulsifying agent, filler, sequestering agent, chelating agent, preserving agent, vitamin, blocker, moisturing agent, essential oil, dye, pigment, hydrophilic or hydrophobic activator, lipid vesicle or other components generally used in cosmetics and skin science The cosmetic composition for recovering skin damage or reproducing skin of the present invention can include, in addition to the *Euphorbia kansui* extract or the fractions thereof, a supplement generally used in the field of cosmetics such as fatty substance, organic solvent, resolvent, concentrate, gelling agent, softener, antioxidant, suspending agent, stabilizer, foaming agent, odorant, surfactant, water, ionic or non-ionic emulsifying agent, filler, sequestering agent, chelating agent, preserving agent, vitamin, blocker, moisturing agent, essential oil, dye, pigment, hydrophilic or hydrophobic activator, lipid vesicle or other components generally used in cosmetology or skin science. The amount of the above supplement can be determined as generally accepted in the field of skin science. The cosmetic composition of the present invention can be prepared in the form of skin lotion, skin softener, skin toner, astringent, lotion, milk lotion, moisture lotion, nutritive lotion, massage cream, nutritive cream, moisture cream, hand cream, essence, nutritive essence, pack, soap, shampoo, cleansing foam, cleansing lotion, cleansing cream, body lotion, body cleanser, emulsion, press powder, loose powder, or eye shadow.

The present invention also provides a health food for recovering skin damage or reproducing skin comprising the *Euphorbia kansui* extract or the fractions thereof as an active ingredient.

The *Euphorbia kansui* extract or the fractions thereof might have the activity of treating wounds, recovering skin damage, or reproducing skin, but not always limited thereto.

The *Euphorbia kansui* extract or the fractions thereof of the present invention induced the phosphorylations of both PKD1 and ERK inducing the activation of epithelial cells on wounded skin and also had the effect of activating cell scattering in addition to the excellent wound-healing effect, so that they can be effectively used as an active ingredient for a health food for recovering skin damage or reproducing skin.

The food herein is not limited. For example, the *Euphorbia kansui* extract can be added to meats, sausages, breads, chocolates, candies, snacks, cookies, pizza, ramyuns, flour products, gums, dairy products including ice cream, soups, beverages, tea, drinks, alcohol drinks and vitamin complex, etc, and in wide sense, almost every food applicable in the production of health food can be included.

The *Euphorbia kansui* extract or the fractions thereof of the present invention can be added as it is or as mixed with other food components according to the conventional method. The mixing ratio of active ingredients can be regulated according to the purpose of use (prevention or health enhancement). In general, to produce health food or beverages, the *Euphorbia kansui* extract or the fractions thereof is added preferably by 0.1~90 weight part. However, if long term administration is required for health and hygiene or regulating health condition, the content can be lower than the above but higher content can be accepted as well since the extract has been proved to be very safe.

The composition for health beverages of the present invention can additionally include various flavors or natural carbohydrates, etc, like other beverages in addition to the *Euphorbia kansui* extract or the fractions thereof. The natural carbohydrates above can be one of monosaccharides such as glucose and fructose, disaccharides such as maltose and sucrose, polysaccharides such as dextrin and cyclodextrin, and sugar alcohols such as xilytole, sorbitol and erythritol. Besides, natural sweetening agents (thaumatin, stevia extract, for example rebaudioside A, glycyrrhizin, etc.) and synthetic sweetening agents (saccharin, aspartame, etc.) can be included as a sweetening agent. The content of the natural carbohydrate is preferably 1~20 g and more preferably 5~12 g in 100 ml of the composition.

In addition to the ingredients mentioned above, the *Euphorbia kansui* extract or the fractions thereof of the present invention can include in a variety of nutrients, vitamins, minerals (electrolytes), flavors including natural flavors and synthetic flavors, coloring agents and extenders (cheese, chocolate, etc.), pectic acid and its salts, alginic acid and its salts, organic acid, protective colloidal viscosifiers, pH regulators, stabilizers, antiseptics, glycerin, alcohols, carbonators which used to be added to soda, etc. The *Euphorbia kansui* extract or the fractions thereof of the present invention can also include natural fruit juice, fruit beverages and/or fruit flesh addable to vegetable beverages.

All the mentioned ingredients can be added singly or together. The mixing ratio of those ingredients does not matter in fact, but in general, each can be added by 0.1~20 weight part per 100 weight part of the *Euphorbia kansui* extract or the fractions thereof of the present invention.

The present invention further provides a method for treating wounds or reproducing skin containing the step of administering the *Euphorbia kansui* extract or the fractions thereof to a subject.

The present invention also provides a use of the *Euphorbia kansui* extract or the fractions thereof for a pharmaceutical composition for treating wounds or reproducing skin.

The present invention also provides a use of the *Euphorbia kansui* extract or the fractions thereof for a cosmetic composition for recovering skin damage or reproducing skin.

The present invention also provides a use of the *Euphorbia kansui* extract or the fractions thereof for a health food for recovering skin damage or reproducing skin.

The *Euphorbia kansui* extract or the fractions thereof of the present invention induced the phosphorylations of both PKD1 and ERK inducing the activation of epithelial cells on wounded skin and also had the effect of activating cell scattering in addition to the excellent wound-healing effect, so that they can be effectively used as an active ingredient for a pharmaceutical composition for treating wounds and reproducing skin, a cosmetic composition or a health food for recovering skin damage or reproducing skin.

The present invention also provides a pharmaceutical composition for treating wounds or reproducing skin comprising the diterpene compound represented by formula 1 or formula 2 or the pharmaceutically acceptable salts thereof as an active ingredient.

The present invention also provides a cosmetic composition for recovering skin damage or reproducing skin comprising the diterpene compound represented by formula 1 or formula 2 or the pharmaceutically acceptable salts thereof as an active ingredient.

The present invention also provides a health food for recovering skin damage or reproducing skin comprising the diterpene compound represented by formula 1 or formula 2 or the pharmaceutically acceptable salts thereof as an active ingredient.

[Formula 1]

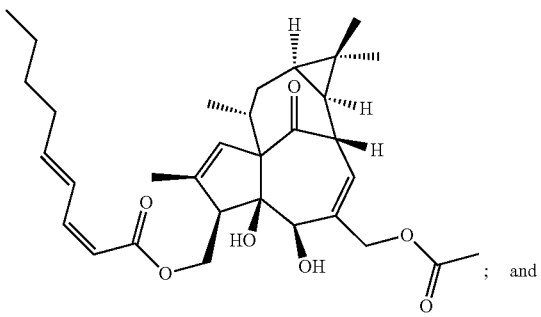

KC73-2

; and

[Formula 2]

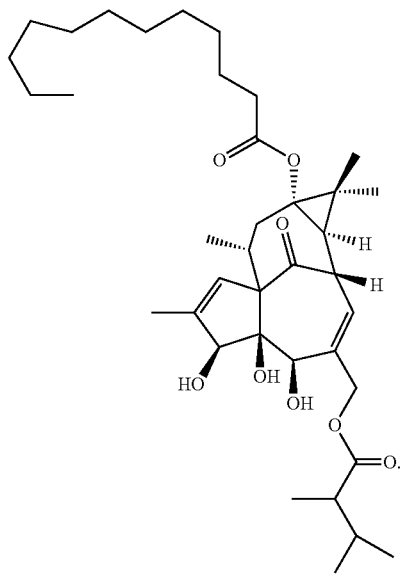

KC16-20

The diterpene compound represented by formula 1 or formula 2 can be the one isolated from the *Euphorbia kansui* extract, but not always limited thereto.

The said compound is supposed to have the activity of treating wounds, recovering skin damage, or reproducing skin by inducing the activation of epithelial cells, but not always limited thereto.

In a preferred embodiment of the present invention, the compound represented by formula 1 or formula 2 was isolated from the *Euphorbia kansui* extract by chromatography fractionation, followed by the investigation of the structure (see formula 1 and formula 2).

The diterpene compound represented by formula 1 or formula 2 of the present invention induced the phosphorylations of both PKD1 and ERK inducing the activation of epithelial cells on wounded skin and also had the effect of activating cell scattering in addition to the excellent wound-healing effect, so that it can be effectively used as an active ingredient for a pharmaceutical composition for treating wounds and reproducing skin, a cosmetic composition or a health food for recovering skin damage or reproducing skin.

The present invention also provides a method for treating wounds or reproducing skin containing the step of administering a pharmaceutically effective dose of the diterpene compound represented by formula or formula 2 or the pharmaceutically acceptable salts thereof to a subject with skin damage.

The present invention also provides a use of the diterpene compound represented by formula 1 or formula 2 or the pharmaceutically acceptable salts thereof for a pharmaceutical composition for treating wounds or reproducing skin.

The present invention also provides a use of the diterpene compound represented by formula 1 or formula 2 or the pharmaceutically acceptable salts thereof for a health food for recovering skin damage or reproducing skin.

In addition, the present invention provides a use of the diterpene compound represented by formula 1 or formula 2 or the pharmaceutically acceptable salts thereof for a cosmetic composition for recovering skin damage or reproducing skin.

The diterpene compound represented by formula 1 or formula 2 of the present invention induced the phosphorylations of both PKD1 and ERK inducing the activation of epithelial cells on wounded skin and also had the effect of activating cell scattering in addition to the excellent wound-healing effect, so that it can be effectively used as an active ingredient for a pharmaceutical composition for treating wounds and reproducing skin, a cosmetic composition or a health food for recovering skin damage or reproducing skin.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of the *Euphorbia kansui* Extract

The *Euphorbia kansui* extract was prepared from the stems or leaves of *Euphorbia kansui* according to the informed protocol (Planta Med 2010; 76(14): 1544-1549). 20 kg of the dried *Euphorbia kansui* stems (Chilsungsa, China) were added to 20 liter of 100% methanol (SK Chemicals, Korea), followed by extraction. As a result, 1.0 kg of the *Euphorbia kansui* methanol extract was prepared.

Example 2

Preparation of the fractions of the *Euphorbia kansui* Extract 1.0 kg of the *Euphorbia kansui* methanol extract prepared in the above example was suspended in 1.5 liter of water, followed by serial extraction using 1.5 liter of acetone, ethyl acetate, chloroform, butyl acetate, 1,3-butyleneglycol, hexane, or diethylether. In this example, 4.0 g of acetone fraction, 4.5 g of ethyl acetate fraction, 230 g of chloroform fraction, 41 g of butyl acetate fraction, 35 g of 1,3-butyleneglycol fraction, 20 g of hexane fraction, and 25 g of diethylether fraction were obtained.

Example 2

Isolation and Purification of the Diterpene Compound from the *Euphorbia kansui* Extract The active compound was confirmed in stems or leaves of *Euphorbia kansui*, and 10 g of the compound was obtained. The compound was purified from the fruit extract by chromatography fractionation and the structure thereof was analyzed (Planta Med 2010; 76(14): 1544-1549). As a result, the compound was confirmed to have the structure represented by the following formula 1 or 2.

[Formula 1]

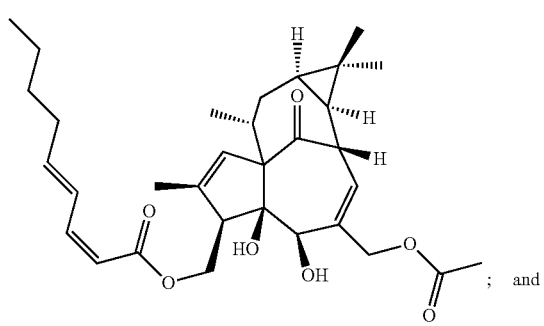

KC73-2; and

[Formula 2]

KC16-20

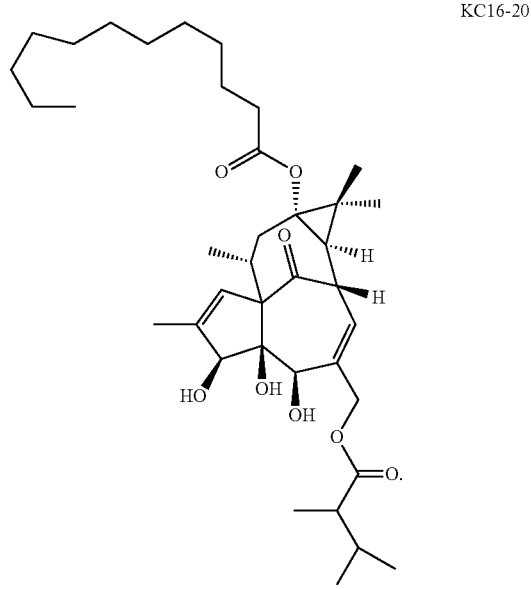

Example 4

Cell Culture

The human cell lines HCT116, KM12C, SW620, and COLO205 (American Type Culture Collection, ATCC, Rockville, Md.) were cultured in a 37° C., 5% $CO_2$ incubator. The cell lines were maintained in DMEM (Life Technologies, Karlsruhe, Germany) supplemented with 10% FCS (Fetal Calf Serum, HyClone, Logan, Utah), 2 mM L-glutamate, 100 μg/ml of penicillin, and 100 μg/ml of streptomycin (Life Technologies).

Experimental Example 1

Investigation of the Activity of the *Euphorbia kansui* Extract to Induce Cell Scattering RT-PCR (Reverse Transcriptase Polymerase Chain Reaction) was performed to investigate whether the *Euphorbia kansui* extract (Eupho K1) could induced cell mobility in epithelia cells (HCT116, KM12C, SW620 and Colo205) and also to investigate the changes of mRNA levels in relation to the generation of fibronectin, the intracellular factor inducing cell mobility.

RT-PCR was performed as follows. Total RNA was extracted according to the standard protocol, and cDNA was synthesized by using AccuScript High Fidelity $1^{st}$ Strand cDNA Synthesis Kit (Stratagene) according to the manufacturer's protocol. Second stage RT-PCR was performed by using oligo-dT primer, reverse transcriptase, particularly a set of primers, and Taq polymerase (Takara, Shiga, Japan). 1 μl of the synthesized cDNA was added to 20 μl of PCR mixture composed of 0.5 U ExTaq DNA polymerase, 1× buffer, and mM dNTP mix (Takara), and a specific primer set. PCR amplification was performed using GeneAmp PCR system 2700 (Applied Biosystems, Foster city, CA, USA) as follows: predenaturation at 94° C. for 5 minutes, denaturation at 94° C. for 45 seconds, annealing at 56° C. for 45 seconds, polymerization at 72° C. for 1 minute, 25~40 cycles from denaturation to polymerization, and final extension at 72° C. for 7 minutes. PCR primers listed in Table 1 were purchased from Bioneer Co (KOREA).

TABLE 1

PCR primers used in cDNA amplification

| Name | Forward | Reverse |
| --- | --- | --- |
| GAPDH | CCATCACCATCTTCCAGGAG | ACAGTCTTCTGGGTGGCAGT |
| Fibronectin | CGGGAATCTTCTCTGTCAGC | GCCATGACAATGGTGTGAAC |
| Zeb1 | GCACCTGAAGAGGACCAGAG | GTGTAACTGCACAGGGAGCA |

PCR product obtained above was electrophoresed on 1.5% agarose gel, and then stained with EtBr (Ethidium Bromide), followed by visualization with Gel Doc 2000 UV trans-illuminator (Bio-Rad Laboratories, Hercules, Calif., USA). Analysis was performed by using quantitative one software (Bio-Rad Laboratories). Each sample was tested in triplicate and the representative data were showed.

Cells were cultured in the presence of 1 ug/ml of the *Euphorbia kansui* extract for 6 hours. The cells were lysed and RNA was extracted therefrom. CDNA was synthesized from the extracted RNA using poly A+ primer and reverse transcriptase. The primers specifically designed for fibronectin and Zeb1 were used for PCR amplification (Table 1). GAPDH was used as the internal control.

When the *Euphorbia kansui* extract was treated to the epithelial cells, HCT116, KM12C, SW620, and Colo205, the fibronectin transcript was most clearly changed in SW620 treated with the *Euphorbia kansui* extract (Eupho K1) (FIG. 1).

Figure 2:
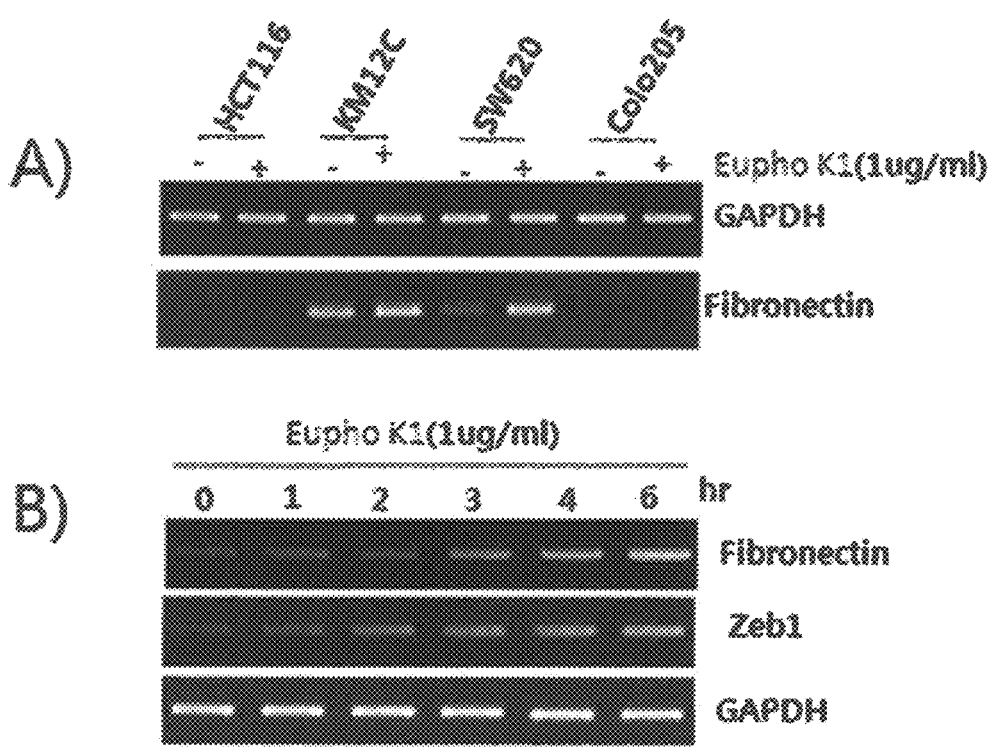
FIG. 2 is a set of diagrams illustrating that the expression of fibronectin was increased in relation to the cell migration promoted in KM12c and SW620, the epithelial cells, treated with the *Euphorbia kansui* extract (FIG. 2A) and this increase continued over the time (FIG. 2B).

The *Euphorbia kansui* extract was treated to SW620, followed by analysis over the time. As a result, the fibronectin transcript was increased after three hours from the treatment and this increase was continued until 6 hours after the treatment. The expression pattern of Zeb1, the E-cadherin transcription inhibitor, related to the inhibition of epithelial cell mobility was also investigated. As a result, it was confirmed that the expression pattern of Zeb1 was similar to the expression pattern of fibronectin transcript (FIG. 2).

Experimental Example 2

Investigation of the Activity of the *Euphorbia kansui* Extract to Induce the Phosphorylations of PKD1 and ERK Involved in Epithelial Cell Activity The *Euphorbia kansui* extract was treated to the epithelial cell line SW620 by the same manner as described in experimental example 1. Then, the phosphorylations of PKD1 and ERK involved in the activity of epithelial cells were investigated.

Particularly, the cells treated with the *Euphorbia kansui* extract were lysed in ice using the mixture composed of cold SDS lysis buffer, 50 mM HEPES, 150 mM NaCl, 0.2 mM EDTA, 0.5% NP-40, 0.1% SDS, 1 mM Na3VO4, 10 mM NaF, and complete protein inhibitor cocktail (Roche) for 30 minutes. The lysate was centrifuged at 13,000 rpm for 30 minutes to precipitate the insoluble part in order to separate the soluble solution. The separated cell solution was quantified, followed by electrophoresis using 10~12% SDS-PAGE. Cellular proteins separated on the gel were transcribed on PVDF membrane (Millipore, Billerica, Mass., USA) at 100 V for 2 hours. To confirm the phosphorylated PKD1 and ERK in the cells, the membrane was reacted with the primary antibodies such as poly rabbit anti-PKD1, -phosphoPKD1 (Ser744/748), -ERK, and -phosphoERK IgG (1:1000, Cell signaling Technology, USA) at room temperature for 60 minutes. Then, the membrane was reacted with the secondary antibody horseradish peroxidase peroxidase-conjugated goat anti-rabbit IgG (Santa Cruz Biotechnology, USA) at room temperature for 60 minutes. The quantification of the cellular protein was performed by using poly rabbit anti-PKD1 and -ERK. Upon completion of the immune response, the membrane was reacted with ECL reagent (Millipore, Billerica, Mass., USA), which was then exposed on X-ray film. The phosphorylation of PKC isotype was confirmed by observing the band on the film.

Figure 3:
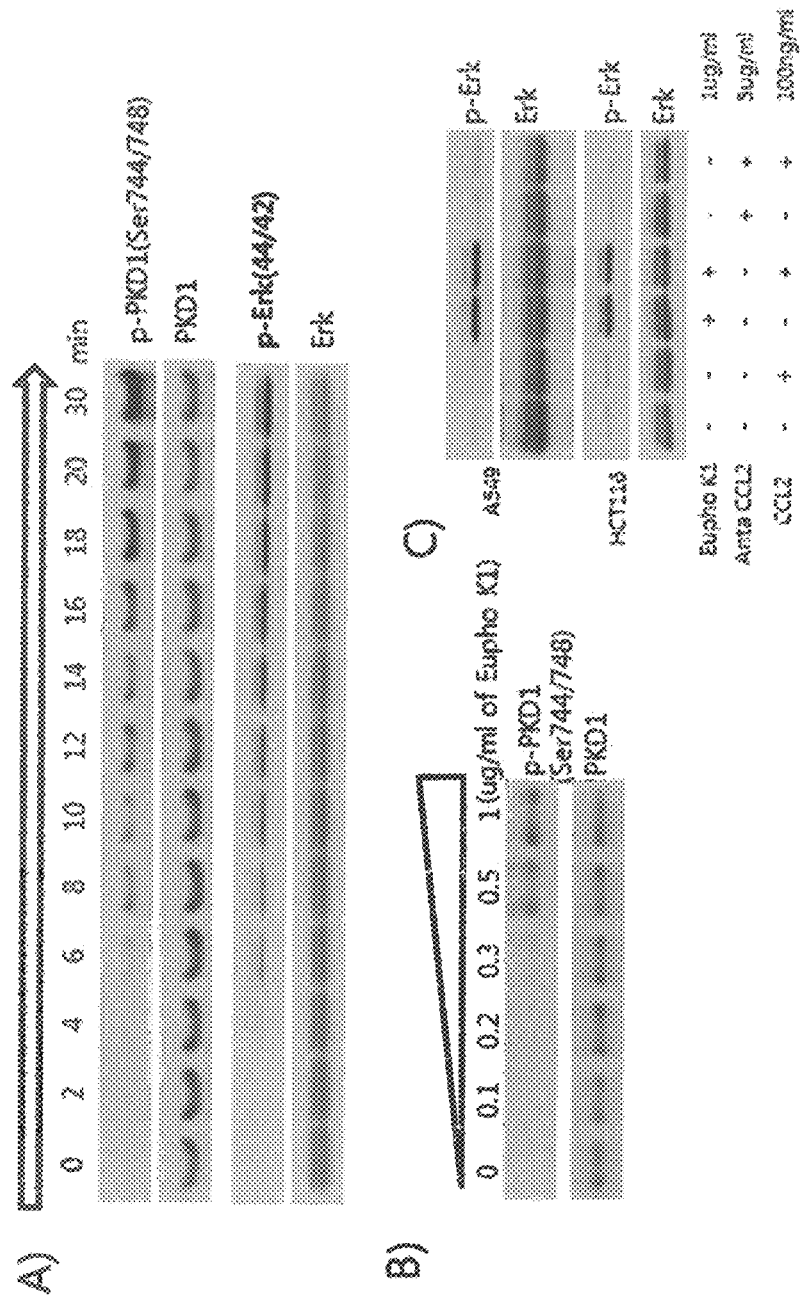
FIG. 3 is a set of diagrams illustrating that the phosphorylations of PKD1 and ERK1 were induced over the treatment time and concentration of the extract in SW620 treated with the *Euphorbia kansui* extract (FIG. 3A and FIG. 3B). The phosphorylation of ERK was observed in other epithelial cells (FIG. 3C).

As a result, the phosphorylations of PKD1 and ERK in the epithelial cell line SW620 were increased for minutes after the treatment with the *Euphorbia kansui* extract time-dependently (FIG. 3A). Titer was observed at the concentration of 0.5 ug/ml (FIG. 3B). The phosphorylation of ERK induced by the *Euphorbia kansui* extract (Eupho K1) was also confirmed in the epithelial cell lines A549 and HCT116. it was confirmed that the *Euphorbia kansui* extract induced the phosphorylation of ERK stronger than CCL2, the ERK phosphorylation related chemokine, used herein as the control (FIG. 3C).

Experimental Example 3

Investigation of the Cell Mobility in Relation to Wound-Healing Induced by the *Euphorbia kansui* Extract <3-1> Cell Mobility Induced by the *Euphorbia kansui* Extract When a wounds is made, the epithelial cells are activated, by which tissue regeneration is induced. The mobility/scattering of the epithelial cells, at this time, is a very important factor to treat the wound.

To measure the cell mobility/scattering, cells were cultured for a day to 80% confluency. On the next day, the cells were scratched in a straight line using a pipette tip and then the floating cells were eliminated. The control group was treated with DMSO. Any changes in the cells of the experimental group treated with the *Euphorbia kansui* extract were observed once a day for two days under microscope and photographed under microscope. Then the cell mobility/scattering was compared.

Figure 4:
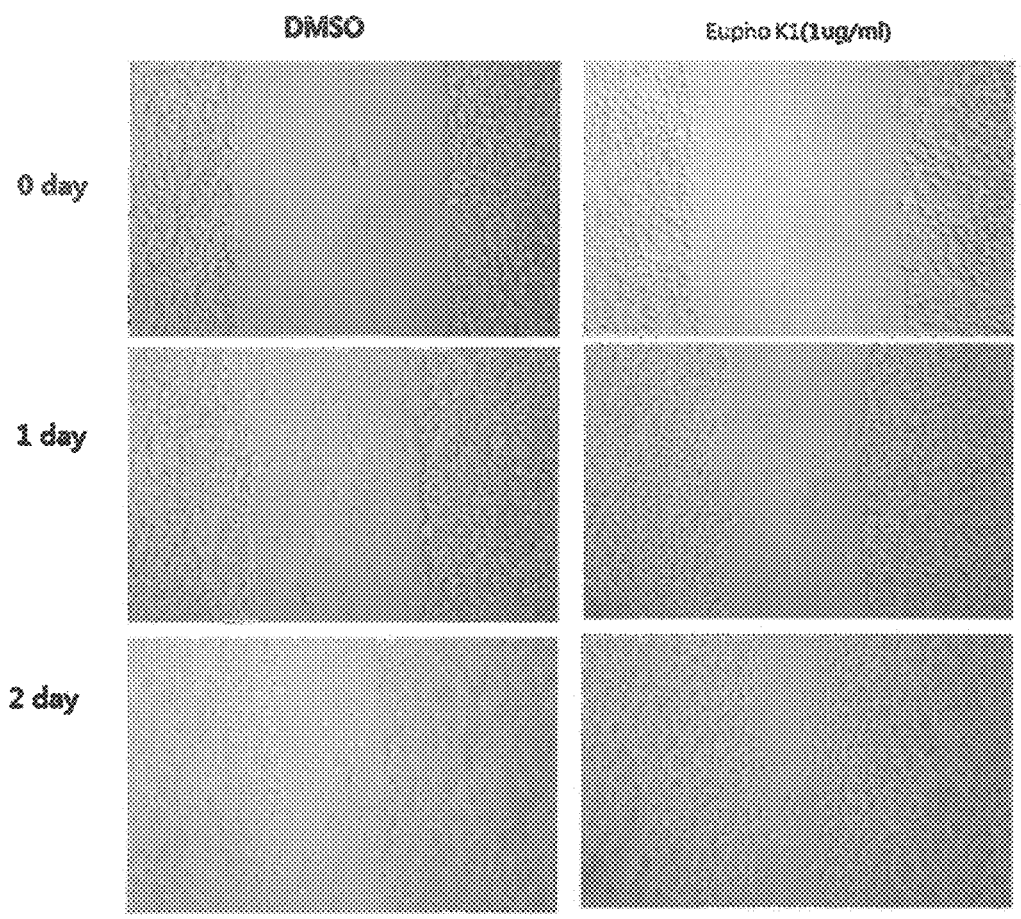
FIG. 4 is a diagram illustrating that the *Euphorbia kansui* extract increased cell migration and had excellent ability to make up the loss of epithelial cells.
Figure 5:
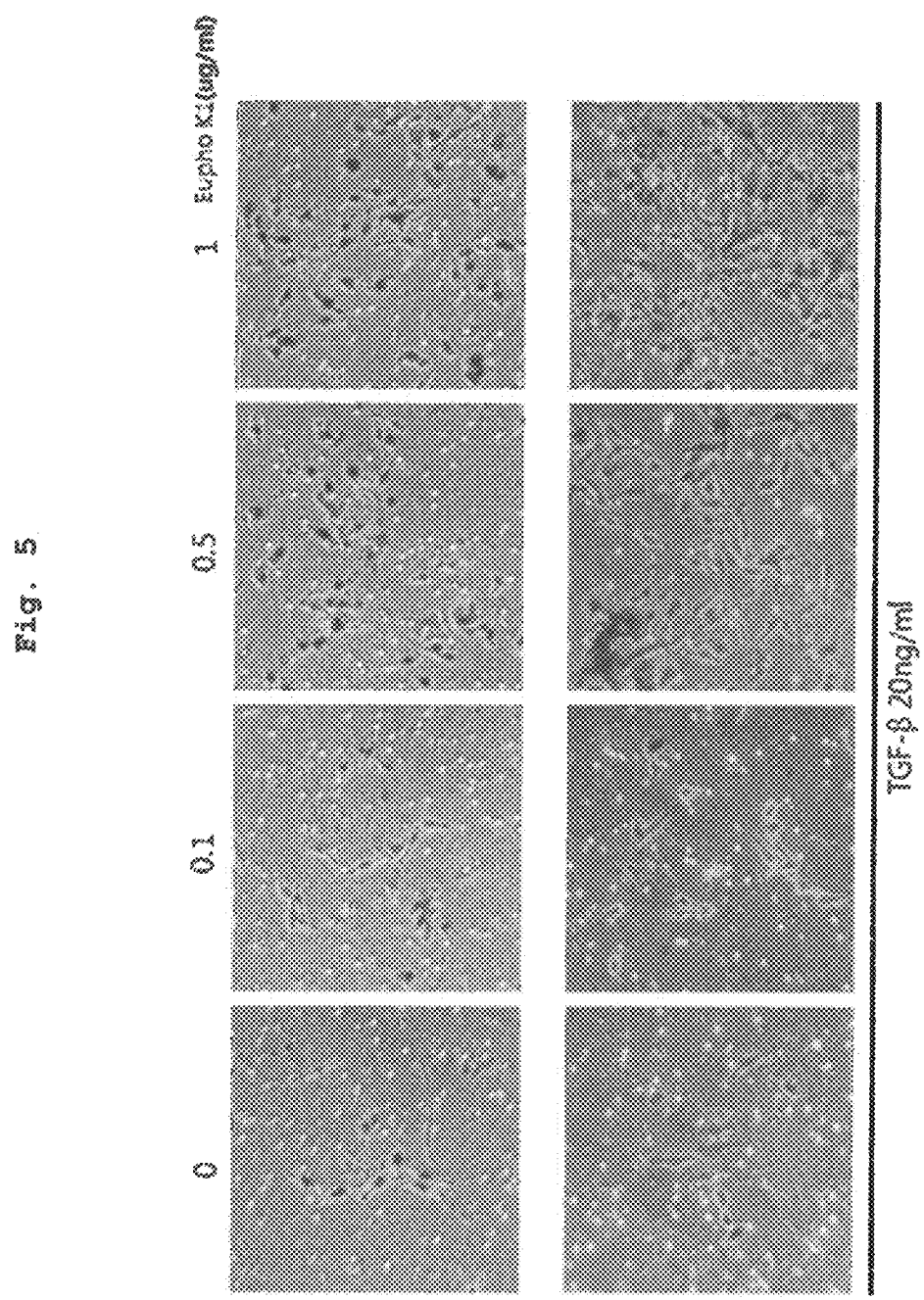
FIG. 5 is a diagram illustrating the effect of the *Euphorbia kansui* extract to increase cell migration. Precisely, the cell migration was maximized in the presence of the *Euphorbia kansui* extract along with TGF-beta, confirmed by matrigel analysis.

As a result, it was confirmed that the *Euphorbia kansui* extract induced cell mobility more effectively than any other active factors (FIG. 4 or FIG. 5). The scattering mediated by cell mobility could fill the loss of epithelial cells more efficiently in the experimental group than in the control group treated with DMSO. Particularly, in the control group treated with DMSO, the loss of cells was filled up 12.5% one day after, and 45% 2 days after. In the meantime, in the cells treated with the *Euphorbia kansui* extract, the loss of cells was filled up 27.8% one day after and 72.3% two days after cell scattering induced, suggesting that a powerful cell mobility was induced (FIG. 4).

<3-2> Analysis of the Wound Healing Activity of the *Euphorbia kansui* Extract

When a wounds is made, the epithelial cells are activated, by which tissue regeneration is induced. This is one of the most peculiar activities of various cytokines (TGF, PDGF, FDF, etc) which are secreted when a wound is made.

Matrigel analysis was performed to evaluate the revitalization of cells in trans well.

Particularly, matrigel (Becton-Dickinson, USA) was diluted in cold medium at the concentration of 20%, which was distributed on the upper part of 24-trans well (Costar, USA), followed by coating at 37° C. for 2~3 hours. Cells were cultured on that. The cells were treated with the *Euphorbia kansui* extract at different concentrations of 0, 0.1, 0.5, and 1 ug/ml. The lower medium was treated with TGF at the concentration of 2 ng/ml. 48 hours later, the cells that were attached on the upper trans well were wiped out with a cotton bud, followed by staining with crystal violet. The cells that passed through trans well were observed under microscope and the number of those migrated cells were counted.

As a result, the cell mobility was greater in the medium treated with the *Euphorbia kansui* extract. When TGF was co-treated with the extract, the cell mobility was even greater. When the cell mobility induced by TGF alone was presented as 1, the cell mobility induced by the *Euphorbia kansui* extract was 18, 61.8, and 69 respectively over the concentrations of the extract of 0.1. 0.5, and 1 ug/ml (FIG. 5).

Experimental Example 4

Skin Reproducing Effect of the *Euphorbia kansui* Extract

The mice (5 weeks old male Balb/C mice) used for the test were purchased from Central Lab. Animal Inc. (Korea), and then raised without diet restriction for full adaptation. The control group mice were also raised in the same condition. The normal Balb/C mouse was shaved and a wound was made intentionally on the skin by tape strapping. When the *Euphorbia kansui* extract (Eupho K1) was treated to the wounded area, skin recovery and the reproduction of skin to normal skin was faster than that of the control. At this time, the test was performed in duplicate with each group composed of 5 mice.

Figure 6:
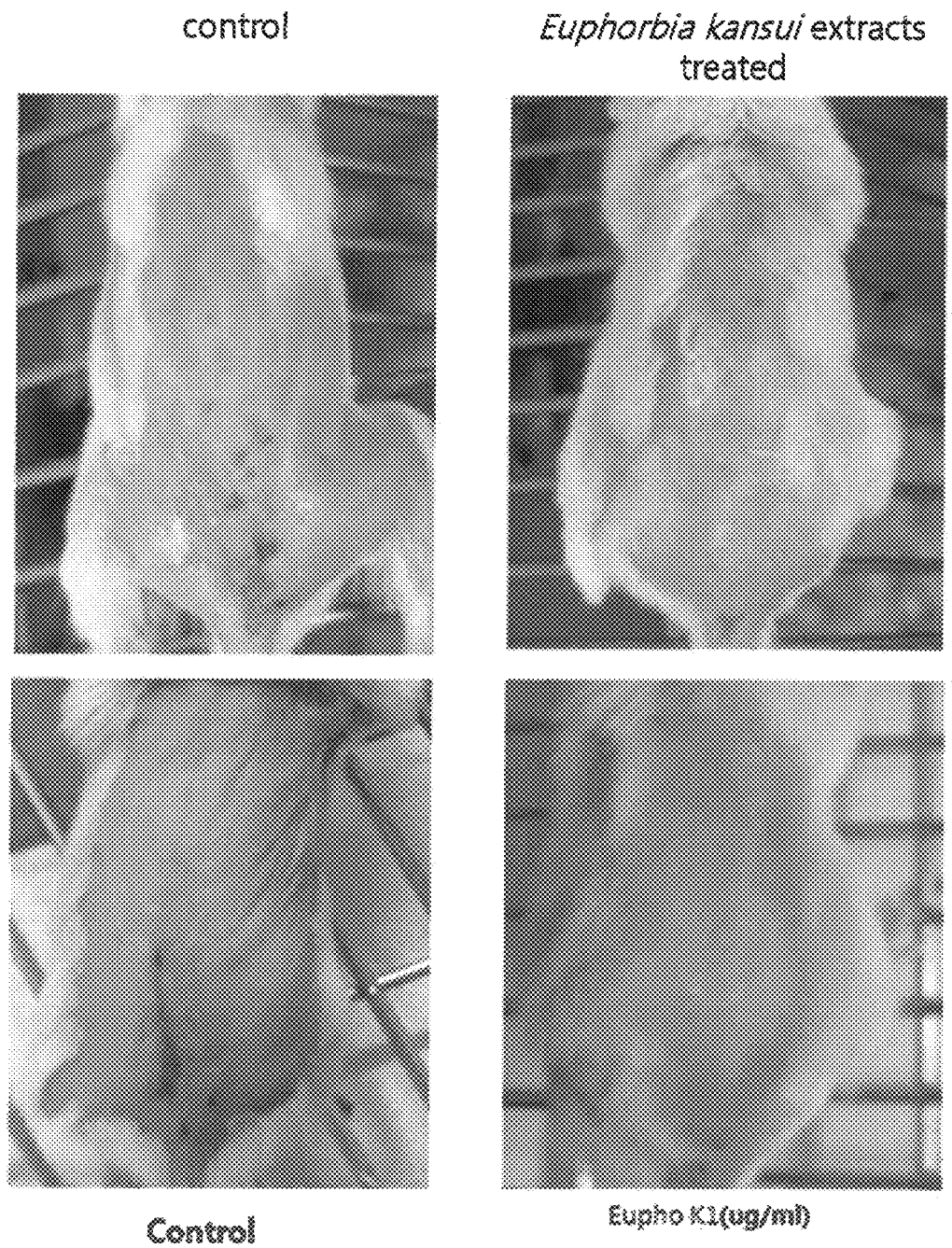
FIG. 6 is a diagram illustrating that the observation of skin reproduction after the treatment of the *Euphorbia kansui* extract in the Balb/C mouse which was shaved on the skin where wounds were made by tape strapping. It was confirmed that the *Euphorbia kansui* extract promoted to recover skin damage and reproduce skin to normal status.

As a result, it was confirmed that the *Euphorbia kansui* extract induced the activation of epithelial cells and was also very effective in wound-healing (FIG. 6).

The Manufacturing Examples of the pharmaceutical preparations comprising the *Euphorbia kansui* extract or the pharmaceutically acceptable salts thereof are described hereinafter.

Manufacturing Example 1

Preparation of Pharmaceutical Formulation

<1-1> Preparation of Powders

| | |
|---|---|
| *Euphorbia kansui* extract | 500 ng |
| Lactose | 1 g |

Powders were prepared by mixing all the above components, which were filled in airtight packs according to the conventional method for preparing powders.

<1-2> Preparation of Tablets

| | |
|---|---|
| *Euphorbia kansui* extract | 500 ng |
| Corn starch | 100 mg |
| Lactose | 100 mg |
| Magnesium stearate | 2 mg |

Tablets were prepared by mixing all the above components by the conventional method for preparing tablets.

<1-3> Preparation of Capsules

| | |
|---|---|
| *Euphorbia kansui* extract | 500 ng |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

<1-4> Preparation of Injectable Solutions

| | |
|---|---|
| *Euphorbia kansui* extract | 500 ng |
| Mannitol | 180 mg |
| $Na_2HPO_4 \cdot 2H_2O$ | 26 mg |
| Distilled water | 2,974 mg |

Injectable solutions were prepared by mixing all the above components by the conventional method for preparing injectable solutions.

The Manufacturing Examples of the cosmetic compositions comprising the *Euphorbia kansui* extract or the pharmaceutically acceptable salts thereof are described hereinafter.

Manufacturing Example 2

Preparation of Cosmetic Composition

<2-1> Preparation of Cream

| | |
|---|---|
| Cetostearyl alcohol | 2.8 weight part |
| Beeswax | 2.6 weight part |
| Stearic acid | 1.4 weight part |
| Glyceryl monostearate, lipophilic | 2 weight part |
| PEG-100 stearate | 1 weight part |
| Sorbitan sesquioleate | 1.4 weight part |
| Jojoba oil | 4 weight part |
| Squalane | 3.8 weight part |
| Polysorbate 60 | 1.1 weight part |
| Macadamia oil | 2 weight part |
| Tocopheryl acetate | 0.2 weight part |
| Methyl polysiloxanes | 0.4 weight part |
| Ethyl paraben | 0.1 weight part |
| Propyl paraben | 0.1 weight part |
| Euxyl K-400 | 0.1 weight part |
| 1,3-butylene glycol | 7 weight part |
| Methyl paraben | 0.05 weight part |
| Glycerin | 6 weight part |
| d-panthenol | 0.2 weight part |
| *Euphorbia kansui* extract | 4.6 weight part |
| Triethanolamine | 0.2 weight part |
| pt 41891 | 0.2 weight part |
| p-$H_2O$ | 46.05 weight part |

<2-2> Preparation of Lotion

| | |
|---|---|
| Cetostearyl alcohol | 1.6 weight part |
| Stearic acid | 1.4 weight part |
| Glyceryl monostearate, lipophilic | 1.8 weight part |
| PEG-100 stearate | 2.6 weight part |
| Sorbitan sesquioleate | 0.6 weight part |
| Squalene | 4.8 weight part |
| Macadamia oil | 2 weight part |
| Jojoba oil | 2 weight part |
| Tocopherol | 0.4 weight part |
| Methyl polysiloxanes | 0.2 weight part |
| Ethyl paraben | 0.1 weight part |
| Propyl paraben | 0.1 weight part |
| 1,3-butylene glycol | 4 weight part |
| Methyl paraben | 0.1 weight part |
| Xanthan gum | 0.1 weight part |
| Glycerin | 4 weight part |
| d-panthenol | 0.15 weight part |
| Allantoin | 0.1 weight part |
| *Euphorbia kansui* extract | 3.5 weight part |
| Carbomers (2% aq. Sol) | 4 weight part |
| Triethanolamine | 0.15 weight part |
| Ethanol | 3 weight part |
| pt 41891 | 0.1 weight part |
| p-$H_2O$ | 48.3 weight part |

Manufacturing Example 3

Preparation of Health Food

<3-1> Preparation of Health Food

| | |
|---|---|
| *Euphorbia kansui* extract | 500 ng |
| Vitamin complex | Proper amount |
| Vitamin A acetate | 70 μg |
| Vitamin E | 1.0 mg |
| Vitamin | 0.13 mg |
| Vitamin B2 | 0.15 mg |
| Vitamin B6 | 0.5 mg |
| Vitamin B12 | 0.2 μg |
| Vitamin C | 10 mg |
| Biotin | 10 μg |
| Nicotinic acid amide | 1.7 mg |
| Folic acid | 50 mg |
| Calcium pantothenate | 0.5 mg |
| Mineral complex | Proper amount |
| Ferrous sulphate | 1.75 mg |
| Zinc oxide | 0.82 mg |
| Magnesium carbonate | 25.3 mg |
| Potassium phosphate monobasic | 15 mg |

| | |
|---|---|
| Potassium phosphate dibasic | 55 mg |
| Potassium citrate | 90 mg |
| Calcium carbonate | 100 mg |
| Magnesium chloride | 24.8 mg |

Vitamins and minerals were mixed according to the preferable composition rate for health food. However, the composition rate can be adjusted. The constituents were mixed according to the conventional method for preparing health food and then the composition for health food (ex. health candies, etc) was prepared according to the conventional method.

<3-2> Preparation of Health Beverages

| | |
|---|---|
| *Euphorbia kansui* extract | 500 ng |
| Citric acid | 1000 mg |
| Oligosaccharide | 100 g |
| Maesil (*Prunus mume*) Extract | 2 g |
| Taurine | 1 g |
| Purified water | up to 900 ml |

The above constituents were mixed according to the conventional method for preparing health beverages. The mixture was heated at 85° C. for 1 hour with stirring and then filtered. The filtrate was loaded in 2 liter sterilized containers, which were sealed and sterilized again, stored in a refrigerator until they would be used for the preparation of a composition for health beverages.

The constituents appropriate for favorite beverages were mixed according to the preferred mixing ratio but the composition ratio can be adjusted according to regional and national preferences, etc.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for treating a mammal suffering from a wound on the skin of the mammal comprising topically administering a therapeutically effective amount of an extract of the stems or leaves of *Euphorbia kansui* to the skin of the mammal to effectively treat the wounds on the skin of the mammal, wherein the extract is obtained by using an organic solvent selected from the group consisting of ethyl acetate, chloroform, butyl acetate, hexane, and diethyl ether.

* * * * *